United States Patent

Kageyama et al.

[11] Patent Number: 5,147,396
[45] Date of Patent: Sep. 15, 1992

[54] INTRAOCULAR LENS

[75] Inventors: Mayumi Kageyama, Akishima; Takeyuki Sawamoto, Tokyo; Niro Tarumi, Akishima; Hiroshi Sakai, Kodaira, all of Japan

[73] Assignee: Hoya Corporation, Tokyo, Japan

[21] Appl. No.: 327,701

[22] Filed: Mar. 23, 1989

[30] Foreign Application Priority Data

Mar. 28, 1988 [JP] Japan .................................. 63-73559

[51] Int. Cl.$^5$ ................................................ A61F 2/16
[52] U.S. Cl. .................................... 623/6; 351/160 H; 523/113
[58] Field of Search ....................... 623/6; 351/160 H; 523/113; 522/26, 99, 50; 528/31, 32

[56] References Cited

U.S. PATENT DOCUMENTS

| | | | |
|---|---|---|---|
| 4,143,949 | 3/1979 | Chen | 351/160 H |
| 4,153,641 | 5/1979 | Deichert | 351/160 H X |
| 4,537,943 | 8/1985 | Talcott | 528/31 X |
| 4,582,884 | 4/1986 | Ratkowski | 528/32 X |
| 4,740,533 | 4/1988 | Su et al. | 528/32 X |
| 4,795,461 | 1/1989 | Lindquist et al. | 623/6 |
| 4,803,254 | 2/1989 | Dunks et al. | 623/6 X |
| 4,872,877 | 10/1988 | Tiffany | 623/6 |

Primary Examiner—Alan W. Cannon
Attorney, Agent, or Firm—Nixon & Vanderhye

[57] ABSTRACT

An intraocular lens whose optic or optic and haptic are composed of a substantially soft polymer obtained by curing a composition comprising:
(a) a dimethylsiloxane-phenylsiloxane copolymer having a vinyl group at each of the both terminals of the molecular chain,
(b) a diorganopolysiloxane having at least three hydrosilyl groups in the molecule, and
(c) an U.V. absorber.

The intraocular lens obtained above has good intraocular stability, excellent biocompatibility, high optical properties and an U.V. absorbability closer to that of the human lens.

By further incorporating a filler as the component (d), the intraocular lens has improved mechanical properties and higher intraocular stability.

14 Claims, No Drawings

INTRAOCULAR LENS

BACKGROUND OF THE INVENTION (1) Field of the Invention

The present invention relates to an intraocular lens, more particularly to a soft silicone intraocular lens having a high refractive index and an ultraviolet absorbability closer to that of the human lens.

(2) Prior Art

As the material for intraocular lenses, there has been mainly used polymethyl methacrylate (hereinafter referred to as PMMA) as described in, for example, Japanese Patent Application Kokai (Laid-Open) No. 59444/1978. With intraocular lenses made of a hard material represented by PMMA, however, various problems cannot be overcome such as (1) these lenses give a strong mechanical irritation to the corneal endothelium, uveal tissue and other ocular tissues at the time of or after lens implantation and (2) a size of incision at least equal to the diameter of the optic (ordinarily 6–7 mm) must be formed at the time of lens implantation and thereby delay in physical rehabilitation and postoperative astigmatism are caused.

Hence, studies have been made on an intraocular lens made of a soft material, which gives a weak mechanical irritation to the corneal endothelium, uveal tissue and other ocular tissues and which can be inserted into the eye through an incision smaller than the diameter of the optic. As a result, there was developed an intraocular lens made of a silicone elastomer and then an intraocular lens made of hydrogel, for example, poly-2-hydroxyethyl methacrylate (hereinafter referred to as PHEMA). The silicone intraocular lens described in, for example, U.S. Pat. No. 4573998 has advantages such as (1) being soft and flexible, (2) having good heat resistance and accordingly being autoclavable, which cannot be applied to PMMA intraocular lenses, and (3) having been widely used as a medical material and providing excellent safety. The PHEMA intraocular lens in a hydrogel state after hydration has advantages such as (1) being soft and flexible, (2) being autoclavable similarly to the silicone elastomer, and (3) showing relatively low adsorption for protein, etc.

The human lens has an ability of absorbing an U.V. light which is harmful to the retina. Therefore, in recent years, there have been made attempts to allow an intraocular lens to have an U.V. absorbability in order to protect the retina of a patient to whom an intraocular lens has been implanted. As a result, there was developed a hard PMMA intraocular lens having an U.V. absorbability, as described in, for example, Japanese Patent Application Kokai (Laid-Open) No. 38411/1985.

However, each of the above mentioned soft materials for intraocular lens which were developed in order to solve the problems of the hard materials such as PMMA, has drawbacks. In the case of the silicone elastomer, it is said that since the dimethylpolysiloxane as a main component of the silicone elastomer has a specific gravity fairly smaller than that of PMMA, the intraocular lens made of the silicone elastomer, tends to cause decentration, tilting and dislocation in the eye. Further, the silicone elastomer has a refractive index as low as 1.405 posing a limitation in the optical design of intraocular lens. That is, the radius of curvature necessary for obtaining a desired refractive power is small; as a result, the resulting intraocular lens has a large thickness, is difficult to insert into the eye, and tends to form wrinkles when folded; this makes it difficult to sufficiently utilize the advantage of a soft intraocular lens that the lens can be inserted through an incision smaller than the diameter of the optic.

Furthermore, the silicone elastomer has substantially no U.V. absorbability; therefore, an U.V. absorber must be added in a large amount in order to endow the silicone elastomer with a desired U.V. absorbability; however, it is difficult to uniformly disperse a generally used U.V. absorber in the silicone elastomer because such an U.V. absorber is difficultly soluble in dimethylpolysiloxane.

In the case of PHEMA, it has a low strength and, in some cases, breaks during the surgical operation for inserting an intraocular lens made of PHEMA into the eye. Further, since PHEMA is a hydrogel, the intraocular lens made thereof intakes aqueous humor, which may cause the staining and discoloration due to adhesion and deposition; thus, the intraocular lens made of PHEMA has also a problem in long-term stability in the eye.

In intraocular lenses having an U.V. absorbability, if the lenses contain a large amount of an U.V. absorber, the U.V. absorber which is harmful to the ocular tissues, may dissolve in aqueous humor in an increased amount. In the conventional intraocular lenses comprising PMMA and an U.V. absorber, the amount of the U.V. absorber used has been as high as 0.15% by weight and accordingly the amount of the U.V. absorber dissolving in aqueous humor has been innegligible. When an U.V. absorber has a low solubility in an intraocular lens material to which the absober is to be added and when an intraocular lens comprising said material and said absorber has been implanted into the eye, it is generally thought that the absorber dissolves in aqueous humor in an increased amount and that it may give an adverse effect to the ocular tissues.

SUMMARY OF THE INVENTION

The present invention is intended to solve the above problems of the conventional intraocular lenses. The first object of the present invention is to provide a silicone intraocular lens which is substantially soft and has good intraocular stability, excellent biocompatibility, high optical properties and an U.V. absorbability closer to that of the human lens. The second object of the present invention is to provide an intraocular lens which satisfies the above mentioned requirements and further has improved mechanical properties and higher intraocular stability.

The above first object of the present invention has been achieved by an intraocular lens whose optic or optic and haptic are composed of a substantially soft polymer obtained by curing a composition comprising:

(a) a dimethylsiloxane-phenylsiloxane copolymer having a vinyl group at each of the both terminals of the molecular chain, (b) a diorganopolysiloxane having at least three hydrosilyl groups in the molecule, and (c) an U.V. absorber.

The above second object of the present invention has been achieved by an intraocular lens whose optic or optic and haptic are composed of a substantially soft polymer obtained by curing a composition comprising:

(a) a dimethylsiloxane-phenylsiloxane copolymer having a vinyl group at each of the both terminals of the molecular chain, (b) a diorganopolysiloxane having at least three hydrosilyl groups in the molecule,
(c) an U.V. absorber, and
(d) a filler.

DETAILED DESCRIPTION OF THE INVENTION

The component (a) used in the present invention is a dimethylsiloxane-phenylsiloxane copolymer having a vinyl group at each of the both terminals of the molecular chain. The copolymer forms a main component in a soft silicone elastomer obtained by curing a composition comprising the components (a), (b), (c) and optionally (d). It is a compound represented by either of the following general formulas.

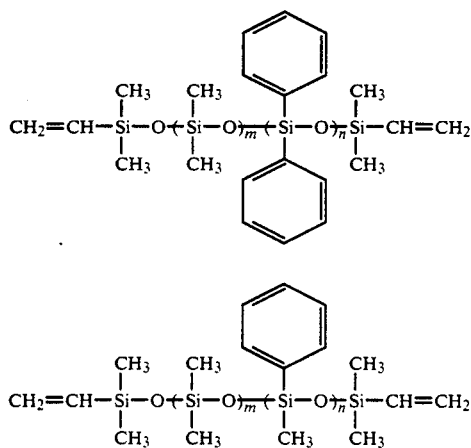

(wherein m is zero or larger and n is one or larger.)

The viscosity of the component (a) varies depending on the molecular weight, but is preferably 100-100,000 cP at 25° C. It is because when the viscosity is smaller than 100 cP, the resulting intraocular lens has too low a polymerization degree and may not have a strength necessary for intraocular lenses and, when the viscosity is larger than 100,000 cP, the molding operation of the resulting intraocular lens is difficult. However, the use of a component (a) having a viscosity larger than 100,000 cP is possible when it is blended with another component (a) of low viscosity.

In the present invention, the phenyl group content in the component (a) is preferably at least 4% of all organic groups. It is because when the phenyl group content is less than 4%, the resulting intraocular lens has too low a refractive index and, in order to have a necessary refractive power, it must be made into a large thickness. For example, when a standard intraocular lens having a diameter of the optic of 6 mm and a refractive power of 20 diopter is intended to produce from a component (a) whose phenyl group content is 3%, the lens inevitably has a thickness about two times that of a PMMA intraocular lens of conventional art.

The phenyl group in the component (a) is also preferably 40% or less of all organic groups. It is because when the phenyl group content is more than 40%, it is difficult to obtain a desired soft polymer. For example, a component (a) with a phenyl group content of 75% is a solid, and its reaction with a component (b) gives no soft polymer.

Next, the component (b) which is a diorganopolysiloxane having hydrosilyl groups, is an essential component because the hydrosilyl groups in the component (b) react with the vinyl groups in the component (a) to cause crosslinking and form a silicone elastomer. In order for the component (b) to sufficiently act as a crosslinking agent, the component (b) must have at least three hydrosilyl groups in the molecule. Even if two components (b) have the same number of hydrosilyl groups in the molecule, the content of hydrosilyl group in molecule differs when they have different molecular weights. The content of hydrosilyl group in molecule is desirably 80% or less of all organic groups.

The molecular structure of the component (b) has no restriction but, as typical examples, there can be mentioned compounds having the following general formula.

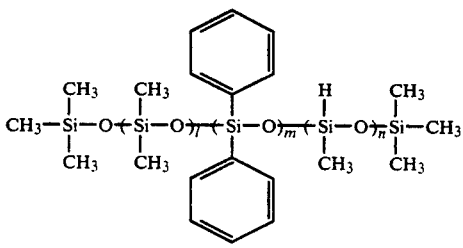

(wherein l and m are each zero or larger and n is three or larger.)

The viscosity of the component (b) varies depending on the molecular weight. There are preferred those compounds having a viscosity of 10-100 cP at 25° C. and the same phenyl group content as the component (a).

In mixing the compounds (a) and (b), it is preferable that the vinyl group in the component (a) and the hydrosilyl group in the component (b) be in a ratio of 1:2 to 1:10, particularly 1:3 to 1:8. It is because when the amount of the hydrosilyl group is less than two times the amount of the vinyl group, curing is insufficient and tackiness remains and, when the hydrosilyl group amount is more than 10 times, the reaction product is fragile and has low mechanical properties.

The component (c) which is an U.V. absorber, is added so that the resulting intraocular lens has a function closer to that of the human lens. As the U.V. absorber used in the present invention, there can be mentioned at least one compound selected from benzotriazole compounds such as 2(2'-hydroxy-5'-methylphenyl)-benzotriazole, 2(2'-hydroxy-3',5'-di-tert-butyl-phenyl)-benzotriazole, 2(2'-hydroxy-3'-tert-butyl-5'-methylphenyl)-5-chlorobenzotriazole, 2(2'-hydroxy-3',5'-di-tertbutylphenyl)-5-chlorobenzotriazole, 2(2'-hydroxy-3',5'-di-tertamylphenyl)benzotriazole, 2(2'-hydroxy-5'-tert-butylphenyl)-benzotriazole, 2(2'-hydroxy-5'-tert-octylphenyl)-benzotriazole and the like, as well as from benzophenone compounds such as 2,4-dihydroxybenzophenone, 2-hydroxy-4-acetoxyethoxybenzophenone, 2-hydroxy-4-methoxybenzophenone, 2,2'-dihydroxy-4-methoxybenzophenone, 2,2'-dihydroxy-4,4'-dimethoxybenzophenone, 2-hydroxy- 4-n-octoxybenzophenone, 2-hydroxy-4-iso-octoxybenzophenone, 2-hydroxy-4-dodecyloxybenzophenone, 2-hydroxy-4-octadecyloxybenzophenone, 2,2'-dihydroxy-4,4'-dimethoxy-5,5'-disulfobenzophenone-disodium, 2-hydroxy-4-(2-hydroxy-3-methacryloxy)propoxybenzophenone and the like. The addition amount of the component (c) is preferably 0.01-1.0% by weight, particularly preferably 0.05–0.7% by weight. When the amount is less than 0.01% by weight, the resulting intraocular lens has no sufficient U.V. absorbability. When the amount is more than 1.0% by weight, the component (c) dissolves in aqueous humor in an undesired amount. As preferable examples of the component (c), there can be mentioned benzotriazole compounds capable of absorbing even an ultraviolet light of longer wavelength. The use of such a compound can exhibit a sufficient effect at a smaller addition amount.

In the present invention, the main component of the silicone elastomer as a base material of intraocular lens contains phenyl groups in the molecule and accordingly has an ability of shielding an ultraviolet light of short wavelength without adding an U.V. absorber. Meanwhile, benzotriazole compounds show the highest absorbability for an ultraviolet light of 290–400 nm but generally have low solubility in resins. Phenyl group-containing silicones can dissolve benzotriazole compounds better than ordinary silicones. These matters are effective in the present invention for reducing the amount of U.V. absorber added as well as the amount of U.V. absorber dissolving in aqueous humor. Thus, the phenyl group-containing silicone is very effective in production of an intraocular lens having an U.V. absorbability.

The polymer obtained by curing a composition comprising the components (a), (b) and (c) is substantially soft and has good intraocular stability, high optical properties, excellent biocompatibility and an U.V. absorbability closer to that of the human lens, and accordingly can be preferably used as an intraocular lens.

In the present invention, a filler as the component (d) can be added when there is required an intraocular lens of improved mechanical properties and higher intraocular stability.

As the filler, there can be used, for example, silica of aerosol state (fumed silica). The filler preferably has an average particle diameter of 50–500 Å, particularly 70–200 Å. When the average particle diameter is smaller than 50 Å, its uniform dispersion in the main component is difficult. When the average particle diameter is larger than 500 Å, the resulting polymer is cloudy. The amount of the filler is preferably 3–30% by weight, particularly 8–20% by weight of the total weight of the resulting composition. When the amount is less than 3% by weight, the effect of improvement in mechanical properties is small. When the amount is more than 30% by weight, the processability of lens is significantly reduced and the resulting intraocular lens is feared to have an adverse effect on the ocular tissues.

In order to improve the dispersibility of fumed silica in base polymer, it is possible to treat the surface of silica, prior to its use, with a silane treating agent (e.g. organosilyl halide) to make the surface hydrophobic.

Next, the curing method employed in production of the intraocular lens of the present invention is described.

Firstly, the component (a), for example, a dimethylsiloxane-diphenylsiloxane copolymer is weighed. Thereto are added a necessary amount of an ultraviolet absorber as the component (c) and, depending upon the requirements for the intraocular lens to be produced, a necessary amount of a filler as the component (d), and they are mixed. The mixing can be effected manually or mechanically. Then, the component (b) and a catalyst are weighed and added. As the catalyst, there is used one ordinarily used in the curing of the above compounds. Specifically, there are used palladium compounds and platinum compounds. The most frequently used catalyst is chloroplatinic acid. The amount of catalyst added can be appropriately determined in view of operation time and curing time.

After the addition of the component (b) and the catalyst, curing can be completed in a short length of time. When a long pot life is required, the addition of an ordinarily used polymerization inhibitor is effective. After the whole mixture has been stirred, deaeration under vacuum is effected. However, natural deaeration is sufficient when the mixture has a low viscosity. Then, the resulting mixture is casted into an appropriate mold for intraocular lens and is cured at room temperature or with heating. Heating can effect curing and molding in a shorter time. The cured product is released from the mold to obtain a desired intraocular lens.

The shape of the intraocular lens can be a two-piece type wherein the optic and the haptic are composed of different materials, or a one-piece type of disc or plate shape wherein the optic and the haptic are integrated.

The present invention is described in more detail below by way of Examples. However, the present invention is in no way restricted to these Examples.

EXAMPLE 1

There were weighed 95 parts by weight of a dimethysiloxane-diphenylsiloxane copolymer as the component (a) having a vinyl group at each of the both terminals of the molecular chain, a phenyl group content corresponding to 5% of all organic groups and a viscosity of 500 cP at 25° C., 5 parts by weight of a dimethylsiloxane-methylhydrosiloxane copolymer as the component (b) having 6–7 hydrosilyl groups in the molecule and a viscosity of 10 cP at 25° C (the ratio of the vinyl group in the component (a) and the hydrosilyl group in the component (b)=1:3), 0.10 part by weight of 2(2'-hydroxy-3'-tert-butyl-5'-methylphenyl) -5-chlorobenzotriazole as the component (c) and chloroplatinic acid (a catalyst) of an amount corresponding to 1 ppm (as platinum) of the total weight of (a), (b), (c) and the catalyst. Firstly, the component (a) was mixed with the component (c). Thereto were added the component (b) and the catalyst. They were stirred until the whole mixture became uniform. The uniform mixture was deaerated under vacuum, after which it was cast into an appropriate mold for intraocular lens and cured for 30 minutes at 150° C.

The proportion of each component used is shown in Table 1 and the properties of the resulting intraocular lens are shown in Table 2. The intraocular lens of the present Example had an improved refractive index owing to the possession of phenyl group in the molecule and, in the case of a planoconvex shape having an optic diameter of 6 mm and a refractive power of 20 diopter, it had a small lens thickness of 1.0 mm which was sufficient for the proper functioning of soft intraocular lens. The intraocular lens, owing to the addition of an U.V. absorber, also had an U.V. absorbability closer to that of the human lens.

The intraocular lens obtained in Example 1 was subjected to extraction by methanol for 24 hours at 37° C. The amount of U.V. absorber dissoved in methanol was 18 μg when determined by U.V. spectrum.

The same extraction test was conducted for a conventional PMMA intraocular lens having about the same U.V. absorbability as the lens of Example 1, and the amount of U.V. absorber dissolved in methanol was 82

μg when determined by U.V. spectrum. This confirmed that the intraocular lens of the present invention was lower in amount of U.V. absorber dissolved and higher in safety.

EXAMPLES 2-5

Components shown in Table 1 were mixed with chloroplatinic acid (a catalyst) of an amount corresponding to 1 ppm (as platinum) of the total weight of the components and chloroplatinic acid and cured in accordance with the same procedure as in Example 1. The properties of the resulting intraocular lenses are shown in Table 2. Each of the lenses showed effects at least equal to Example 1.

EXAMPLE 6

There were weighed 83 parts by weight of a dimethylsiloxane-diphenylsiloxane copolymer as the component (a) having a vinyl group at each of the both terminals of the molecular chain, a phenyl group content corresponding to 15% of all organic groups and a viscosity of 500 cP at 25° C, 7 parts by weight of a dimethylsiloxane-methylhydrosiloxane copolymer as the component (b) having 6-7 hydrosilyl groups in the molecule and a viscosity of 10 cP at 25° C (the ratio of the vinyl group in the component (a) and the hydrosilyl group in the component (b)=1:5), 0.14 part by weight of 2(2'-hydroxy-5'-methylphenyl)benzotriazole as the component (c), 10 parts by weight of silica of aerosol state (fumed silica) as the component (d) and chloroplatinic acid (a catalyst) of an amount corresponding to 1 ppm (as platinum) of the total amount of the components (a), (b), (c) and (D) and chloroplatinic acid. Firstly, the component (a) was thoroughly mixed with the component (c) and (d). Thereto were added the component (b) and the catalyst, and they were stirred until the whole mixture became uniform. The uniform mixture was deaerated under vacuum, after which it was cast into an appropriate mold for intraocular lens and cured for 30 minutes at 150° C. The proportion of each component used is shown in Table 1, and the properties of the resulting intraocular lens are shown in Table 2. The intraocular lens of the present Example had an improved refractive index owing to the possession of phenyl group in the molecule and an U.V. absorbability closer to that of the human lens owing to the addition of an U.V. absorber. In addition, the intraocular lens had a significantly improved break strength owing to the addition of a filler.

EXAMPLES 7-10

The components shown in Table 1 were mixed with chloroplatinic acid (a catalyst) of an amount corresponding to 1 ppm (as platinum) of the total amount of the components and chloroplatinic acid and cured in accordance with the procedure of Example 6. The properties of the resulting intraocular lenses are shown in Table 2. Each of the lenses showed effects at least equal to those of Example 6.

COMPARATIVE EXAMPLE 1

Each component was mixed with chloroplatinic acid (a catalyst) of an amount corresponding to 1 ppm (as platinum) of the total amount of the components and chloroplatinic acid and cured in the same procedure as in Example 1 except that the component (a) was replaced by a dimethylpolysiloxane containing no phenyl group and there was used no component (c). The properties of the resulting intraocular lens are shown in Table 2. The lens had a low refractive index of 1.41; therefore, in the case of a planoconvex shape having an optic diameter of 6 mm and a refractive power of 20 diopter, the lens thickness was 1.7 mm. This thickness is an increase of 70% as compared with that of Example 1 and makes difficult the lens insertion into the eye through a small incision which is an advantage of soft intraocular lens. Further, the lens of this Comparative Example had a lower break strength than any of the Examples. Furthermore, the lens transmitted an ultraviolet light of up to about 200 nm and had a poor U.V. absorbability.

COMPARATIVE EXAMPLE 2

Each component was mixed with chloroplatinic acid of an amount corresponding to 1 ppm (as platinum) of the total amount of the components and chloroplatinic acid and cured in the same procedure as in Example 5 except that the component (a) was replaced by a dimethylpolysiloxane containing no phenyl group. However, 2(2'-hydroxy-5'-methylphenyl)benzotriazole as the component (c) had difficultly soluble in the dimethylsiloxane and part of the component (c) remained undissolved. As a result, the mixture was cloudy as a whole and was not transparent and it was difficult to obtain an intraocular lens. Hence, 2(2'-hydroxy-5'-tert-octylphenyl)benzotriazole was used as the component (c) and there was prepared an intraocular lens having about the same U.V. absorbability as that of Example 5. In this case, the amount of the component (c) required was as high as 0.30 part by weight, which was more than two times the amount of Example 5.

TABLE 1

| | Component (a) | | | | Component (b) | | | | | Component (c) | | Component (d) | |
|---|---|---|---|---|---|---|---|---|---|---|---|---|---|
| | Structure*1 | Content of phenyl group (%) | Viscosity at 25° C. (cP) | Parts by weight | Structure*1 | Viscosity at 25° C. (cP) | Number of hydrosilyl group (Si—H) in molecule | Parts by weight | Ratio*2 | Compound*3 | Parts by weight | Particle diameter (Å) | Parts by weight |
| Example 1 | $S_P 1$ | 5 | 500 | 95 | $S_H 1$ | 10 | 6-7 | 5 | 3 | $B_T 1$ | 0.10 | — | — |
| Example 2 | $S_P 2$ | 10 | 1000 | 95 | $S_H 1$ | 10 | 6-7 | 5 | 5 | $B_T 2$ | 0.06 | — | — |
| Example 3 | $S_P 1$ | 5 | 500 | 92 | $S_H 1$ | 10 | 6-7 | 8 | 5 | $B_T 1$ | 0.06 | — | — |
| Example 4 | $S_P 1$ | 10 | 1000 | 95 | $S_H 1$ | 25 | 8-10 | 5 | 3 | $B_T 1$ | 0.10 | — | — |
| Example 5 | $S_P 2$ | 20 | 10000 | 96 | $S_H 1$ | 10 | 6-7 | 4 | 8 | $B_T 2$ | 0.14 | — | — |
| Example 6 | $S_P 1$ | 15 | 500 | 83 | $S_H 1$ | 10 | 6-7 | 7 | 5 | $B_T 2$ | 0.14 | 160 | 10 |
| Example 7 | $S_P 1$ | 20 | 30000 | 91 | $S_H 1$ | 25 | 8-10 | 4 | 8 | $B_T 3$ | 0.08 | 70 | 5 |
| Example 8 | $S_P 1$ | 10 | 10000 | 87 | $S_H 1$ | 25 | 8-10 | 3 | 5 | $B_T 4$ | 0.10 | 160 | 10 |
| Example 9 | $S_P 1$ | 15 | 1000 | 81 | $S_H 1$ | 10 | 6-7 | 4 | 5 | $B_T 3$ | 0.10 | 70 | 15 |
| Example 10 | $S_P 2$ | 25 | 7000 | 89 | $S_H 2$ | 25 | 8-10 | 6 | 8 | $B_T 5$ | 0.06 | 160 | 5 |
| Comparative Example 1 | $S_O$ | — | 500 | 95 | $S_H 1$ | 10 | 6-7 | 5 | 3 | — | — | — | — |
| Comparative | $S_O$ | — | 10000 | 96 | $S_H 1$ | 10 | 6-7 | 4 | 8 | $B_T 4$ | 0.30 | — | — |

TABLE 1-continued

| | Component (a) | | | Component (b) | | | | Component (c) | | Component (d) | |
|---|---|---|---|---|---|---|---|---|---|---|---|
| | Structure*1 | Content of phenyl group (%) | Viscosity at 25° C. (cP) | Parts by weight | Structure*1 | Viscosity at 25° C. (cP) | Number of hydrosilyl group (Si—H) in molecule | Parts by weight | Ratio*2 | Compound*3 | Parts by weight | Particle diameter (Å) | Parts by weight |
| Example 2 | | | | | | | | | | | | | |

*1 Each symbol $S_P1$, $S_P2$, $S_H1$, $S_H2$, $S_D$ denotes the following structure.

$S_P1$ $CH_2=CH-Si(CH_3)_2-O-[Si(CH_3)_2-O]_m-Si(C_6H_5)_2-O-[Si(CH_3)_2-O]_n-Si(CH_3)_2-CH=CH_2$ $S_P2$ $CH_2=CH-Si(CH_3)_2-O-[Si(CH_3)_2-O]_m-Si(C_6H_5)_2-O-[Si(CH_3)_2-O]_n-Si(CH_3)_2-CH=CH_2$ (with H on center Si)

$S_H1$ $CH_3-Si(CH_3)_2-O-[Si(CH_3)_2-O]_m-Si(H)(CH_3)-O-Si(C_6H_5)_2-O-Si(H)(CH_3)-O-[Si(CH_3)_2-O]_n-Si(CH_3)_3$ $S_D$ $CH_2=CH-Si(CH_3)_2-O-[Si(CH_3)_2-O]_n-Si(CH_3)_2-CH=CH_2$

*2 Ratio is a number of all hydrosilyl groups in the component (b) when the number of all vinyl groups in the component (a) is taken as 1.

*3 Each symbol ($B_T1$, $B_T2$, $B_T3$, $B_T4$, $B_T5$) denotes the following compound.
$B_T1$: 2(2'-Hydroxy-3'-tert-butyl-5'-methylphenyl)-5-chlorobenzotriazole
$B_T2$: 2(2'-Hydroxy-5'-methylphenyl)benzotriazole
$B_T3$: 2(2'-Hydroxy-3',5'-di-tert-butylphenyl)benzotriazole
$B_T4$: 2(2'-Hydroxy-5'-tert-octylphenyl)benzotriazole
$B_T5$: 2(2'-Hydroxy-3',5'-di-tert-butylphenyl)-5-chlorobenzotriazole

TABLE 2

|  | Refractive index*4 (25° C.) | Break strength*5 (g/mm²) | Wavelength of U.V. absorbed*6 (nm) | Wavelength of U.V. absorbed*7 (nm) |
| --- | --- | --- | --- | --- |
| Example 1 | 1.43 | 291 | 406 | 385 |
| Example 2 | 1.44 | 363 | 410 | 400 |
| Example 3 | 1.43 | 334 | 400 | 367 |
| Example 4 | 1.44 | 347 | 406 | 382 |
| Example 5 | 1.47 | 392 | 420 | 410 |
| Example 6 | 1.46 | 548 | 424 | 412 |
| Example 7 | 1.47 | 726 | 398 | 383 |
| Example 8 | 1.44 | 713 | 393 | 369 |
| Example 9 | 1.46 | 679 | 393 | 371 |
| Example 10 | 1.49 | 689 | 406 | 367 |
| Comparative Example 1 | 1.41 | 165 | 225 | <200 |
| Comparative Example 2 | 1.41 | 280 | 415 | 384 |

*4 A refractive index at 25° C. was measured by an Abbe's refractometer manufactured by Atago Co.
*5 Measured using a sample of 0.2 mm in thickness and 0.5 mm in width.
*6 Wavelength of U.V. absorbed was taken as an U.V. wavelength which gave a transmittance of 50% when a sample of 1 mm in thickness was measured for transmittance in a physiological saline solution using a recording spectrophotometer.
*7 Wavelength of U.V. absorbed was taken as an U.V. wavelength which gave a transmittance of 1% when a sample of 1 mm in thickness was measured for transmittance in a physiological saline solution using a recording spectrophotometer.

The soft silicone intraocular lens of the present invention comprising a dimethylsiloxane-phenylsiloxane as a main component, a diorganopolysiloxane and an U.V. absorber, is soft and flexible, has good intraocular safety, gives low mechanical irritation to the corneal enthothelium, uveal tissue and other ocular tissues, and has excellent biocompatibility. Further, the intraocular lens has a high refractive index and accordingly can be processed so as to have a small thickness. Furthermore, in the intraocular lens, since the solubility of the U.V. absorber in the soft silicone is improved, the U.V. absorber is uniformly dispersed and accordingly is unlikely to dissolve in aqueous humor, and the intraocular lens has a sufficient U.V. absorbability at a very small addition amount of an U.V. absorber.

In addition, the intraocular lens of the present invention can possess an improved mechanical strength and improved intraocular stability when a filler is added.

What is claimed is:

1. An intraocular lens whose optic or optic and haptic are composed of a substantially soft polymer obtained by curing a composition comprising:

(a) a dimethylsiloxane-phenylsiloxane copolymer having a vinyl group at each of the two terminals of the molecular chain, (b) a diorganopolysiloxane having at least three hydrosilyl groups in the molecule, and (c) an U.V. absorber.

2. An intraocular lens according to claim 1, wherein the dimethylsiloxane-phenylsiloxane copolymer as the component (a) is a compound represented by either of the following general formulas;

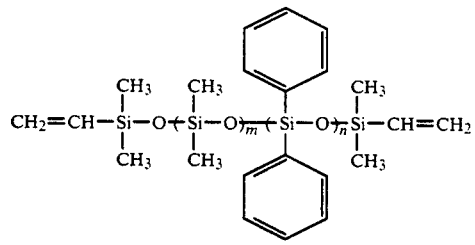

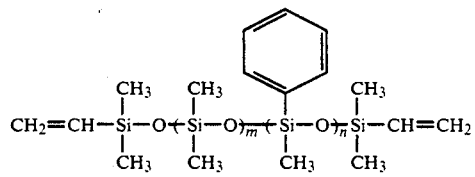

wherein m is zero or larger and n is one or larger.

3. An intraocular lens according to claim 1, wherein the diorganopolysiloxane as the component (b) is a compound represented by the following general formula.

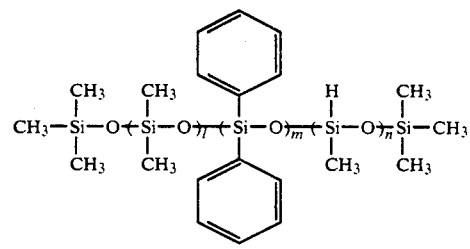

wherein l and m are each zero or larger and n is three or larger.

4. An intraocular lens according to claim 1, wherein the vinyl group in the component (a) and the hydrosilyl group in the component (b) are in a ratio of 1:2 to 1:10.

5. An intraocular lens according to claim 1, wherein the U.V. absorber as the component (c) is at least one compound selected from benzotriazole compounds.

6. An intraocular lens according to claim 1, wherein the the amount of the component (c) is 0.01-1.0% by weight.

7. An intraocular lens whose optic or optic and haptic are composed of a substantially soft polymer obtained by curing a composition comprising:

(a) a dimethylsiloxane-phenylsiloxane copolymer having a vinyl group at each of the two terminals of the molecular chain, (b) a diorganopolysiloxane having at least three hydrosilyl groups in the molecule, (c) an U.V. absorber, and (d) a filler.

8. An intraocular lens according to claim 7, wherein the dimethylsiloxane-phenylsiloxane copolymer as the component (a) is a compound represented by either of the following general formula;

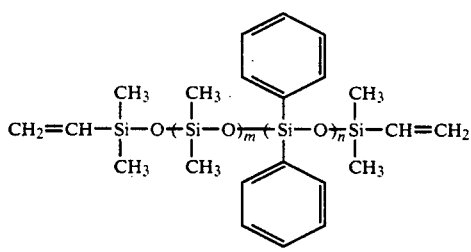

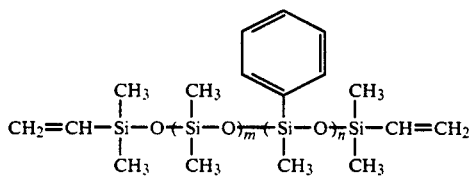

wherein m is zero or larger and n is one or larger.

9. An intraocular lens according to claim 7, wherein the diorganopolysiloxane as the component (b) is a compound represented by the following general formula.

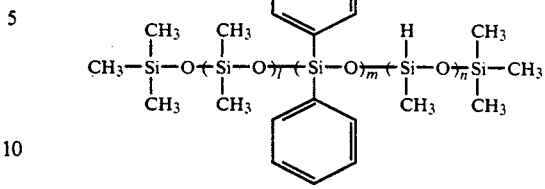

wherein l and m are each zero or larger and n is three or larger.

10. An intraocular lens according to claim 7, wherein the vinyl group in the component (a) and the hydrosilyl group in the component (b) are present in a ratio of 1:2 to 1:10.

11. An intraocular lens according to claim 7, wherein the U.V. absorber as the component (c) is at least one component selected from benzotriazole compounds.

12. An intraocular lens according to claim 7, wherein the amount of the component (c) is 0.01 to 1.0% by weight.

13. An intraocular lens according to claim 7, wherein the filler as the component (d) is silica of aerosol state having an average particle diameter of 50-500 Å.

14. An intraocular lens according to claim 7, wherein the addition amount of the component (d) is 3-30% by weight.

* * * * *